United States Patent
Marrow et al.

(10) Patent No.: US 7,505,129 B2
(45) Date of Patent: *Mar. 17, 2009

(54) ON-LINE ANALYSIS OF POLYMER PROPERTIES FOR CONTROL OF A SOLUTION PHASE REACTION SYSTEM

(75) Inventors: David Geoffrey Marrow, Taylor Lake Village, TX (US); Blu Eric Englehorn, Baton Rouge, LA (US); David A. Yahn, Humble, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 211 days.

This patent is subject to a terminal disclaimer.

(21) Appl. No.: 11/473,949

(22) Filed: Jun. 23, 2006

(65) Prior Publication Data
US 2007/0019191 A1 Jan. 25, 2007

Related U.S. Application Data

(60) Provisional application No. 60/702,083, filed on Jul. 22, 2005.

(51) Int. Cl.
*G01J 3/44* (2006.01)
(52) U.S. Cl. ...................................... 356/301
(58) Field of Classification Search .................. 356/301
See application file for complete search history.

(56) References Cited

U.S. PATENT DOCUMENTS

| | | | |
|---|---|---|---|
| 3,725,378 A | 4/1973 | Chamberlin |
| 3,779,712 A | 12/1973 | Calvert et al. |
| 4,175,169 A | 11/1979 | Beals et al. |
| 4,182,810 A | 1/1980 | Willcox |
| 4,243,619 A | 1/1981 | Fraser et al. |
| 4,469,853 A | 9/1984 | Mori |
| 4,540,753 A | 9/1985 | Cozewith et al. |
| 4,543,399 A | 9/1985 | Jenkins, III et al. |

(Continued)

FOREIGN PATENT DOCUMENTS

EP 0 238 796 9/1987

(Continued)

OTHER PUBLICATIONS

K.R. Beebe et al., "*An Introduction to Multivariate Calibration and Analysis*," Analytical Chemistry, vol. 59, No. 17, pp. 1007A-1017A, Sep. 1, 1987.

(Continued)

*Primary Examiner*—Kara E Geisel
(74) *Attorney, Agent, or Firm*—Amy C. Trexler; Kevin M. Faulkner

(57) ABSTRACT

Methods and systems for analysis of the polymerization material of solution polymerization processes are provided. In certain embodiments, the methods and systems subject the polymerization material to Raman spectroscopy analysis. The Raman spectroscopy provides analysis of reaction mixtures and/or product streams in solution polymerization processes. The Raman spectroscopy analysis may include both compositional and characterization analysis of the reaction mixtures and product streams. The spectroscopy results can be used to provide process control feedback to adjust operating parameters of the reactor operations and/or an associated polymerization product handling and finishing processes.

29 Claims, 2 Drawing Sheets

U.S. PATENT DOCUMENTS

| | | | |
|---|---|---|---|
| 4,588,790 A | 5/1986 | Jenkins, III et al. | |
| 4,620,049 A | 10/1986 | Schmidt et al. | |
| 4,621,952 A | 11/1986 | Aronson | |
| 4,888,704 A | 12/1989 | Topliss et al. | |
| 5,096,634 A | 3/1992 | Tsadares et al. | |
| 5,121,337 A | 6/1992 | Brown | |
| 5,151,474 A | 9/1992 | Lange et al. | |
| 5,202,395 A | 4/1993 | Chambon | |
| 5,270,274 A | 12/1993 | Hashiguchi et al. | |
| 5,274,056 A | 12/1993 | McDaniel et al. | |
| 5,352,749 A | 10/1994 | DeChellis et al. | |
| 5,405,922 A | 4/1995 | DeChellis et al. | |
| 5,436,304 A | 7/1995 | Griffin et al. | |
| 5,462,999 A | 10/1995 | Griffin et al. | |
| 5,589,555 A | 12/1996 | Zboril et al. | |
| 5,638,172 A | 6/1997 | Alsmeyer et al. | |
| 5,675,253 A | 10/1997 | Smith et al. | |
| 5,678,751 A | 10/1997 | Buchanan et al. | |
| 5,682,309 A | 10/1997 | Bartusiak et al. | |
| 5,684,580 A * | 11/1997 | Cooper et al. | 356/301 |
| 5,696,213 A | 12/1997 | Schiffino et al. | |
| 5,864,403 A | 1/1999 | Ajji et al. | |
| 5,892,228 A | 4/1999 | Cooper et al. | |
| 5,999,255 A | 12/1999 | Dupee et al. | |
| 6,072,576 A | 6/2000 | McDonald et al. | |
| 6,114,477 A | 9/2000 | Merrill et al. | |
| 6,144,897 A | 11/2000 | Selliers | |
| 6,204,344 B1 | 3/2001 | Kendrick et al. | |
| 6,204,664 B1 | 3/2001 | Sardashti et al. | |
| 6,218,484 B1 | 4/2001 | Brown et al. | |
| 6,228,793 B1 | 5/2001 | Hosaka et al. | |
| 6,239,235 B1 | 5/2001 | Hottovy et al. | |
| 6,281,300 B1 | 8/2001 | Kendrick | |
| 6,380,325 B1 | 4/2002 | Kendrick | |
| 6,405,579 B1 | 6/2002 | Tjahjadi | |
| 6,479,597 B1 | 11/2002 | Long et al. | |
| 6,608,678 B1 * | 8/2003 | Potyrailo et al. | 356/301 |
| 6,673,878 B2 | 1/2004 | Donck | |
| 2002/0156205 A1 | 10/2002 | Long et al. | |
| 2004/0133364 A1 * | 7/2004 | Marrow et al. | 702/30 |
| 2004/0198927 A1 | 10/2004 | Battiste | |
| 2004/0233425 A1 | 11/2004 | Long et al. | |
| 2004/0266959 A1 | 12/2004 | Heslop et al. | |
| 2005/0154155 A1 * | 7/2005 | Battiste | 356/301 |
| 2007/0021586 A1 * | 1/2007 | Marrow et al. | 528/363 |

FOREIGN PATENT DOCUMENTS

| | | | |
|---|---|---|---|
| EP | 0 257 316 B1 | | 3/1988 |
| EP | 0 328 826 | | 8/1989 |
| EP | 0 406 805 | | 1/1991 |
| EP | 0 561 078 | | 9/1993 |
| JP | 02038841 | | 2/1990 |
| WO | WO 94/21962 | | 9/1994 |
| WO | WO 96/41822 | | 12/1996 |
| WO | WO 98/08066 | | 2/1998 |
| WO | WO 99/01750 | | 1/1999 |
| WO | WO 01/09201 | | 2/2001 |
| WO | WO 01/09203 | | 2/2001 |
| WO | WO 03/042646 | * | 5/2003 |
| WO | WO 2004/063234 | | 7/2004 |
| WO | WO 2005/049663 | | 6/2005 |

OTHER PUBLICATIONS

J. M. Tedesco et al., "*Calibration of dispersive Raman Process Analyzers,*" The Society Of Photo-Optical Instrumentation Engineers, vol. 3537, pp. 200-212, 1999.

G.A. Bakken et al., "*Examination of Criteria for Local Model Principal Component Regression,*" Society for Applied Spectroscopy, vol. 51, No. 12, pp. 1814-1822, 1997.

M.L. Myrick et al., "*In Situ Fiber-Optic Raman Spectroscopy of Organic Chemistry in a Supercritical Water Reactor,*" Journal of Raman Spectroscopy, vol. 25, pp. 59-65, 1994.

T. Naes et al., "*Locally Weighted Regression and Scatter Correction for Near-Infraed Reflectance Data,*" Analytical Chemistry, vol. 62, pp. 664-673, 1990.

G.G. Ardell et al., "*Model Prediction for Reactor Control,*" Chemical Engineering Progress, American Institute of Chemical Engineers, vol. 79, No. 6, pp. 77-83, Jun. 1, 1983.

J.J. Zacca et al., "*Modelling of the Liquid Phase Polymerization of Olefins in Loop reactors,*" Chemical Engineering Science, vol. 48, No. 22, pp. 3743-3765, 1993.

L.P. Russo et al., "*Moving-Horizon State Estimation Applied to an Industrial Polymereization Process,*" American Control Conf. Proc., San Diego, CA, 1999.

H. Martens et al., "*Multivariate Calibration,*" Wiley & Sons Ltd., pp. viii-ix, 1989.

*Multivariate Data Analysis for Windows—Version 3.0*, excerpted from Pirouette Software Manual, Exploratory Analysis: Principal Component Analysis, pp. 5-13 through 5-40, 1985-2000.

E.P.C. Lai et al., "*Noninvasive Spectroscopic Detection of Bulk Polymerization by Stimulated Raman Scattering,*" Applied Spectroscopy, vol. 48, No. 8, 1994.

S. Sekulic et al., "*Nonlinear Multivariate Calibration Methods in Analytical Chemistry,*" Analytical Chemistry, vol. 65, No. 19, pp. 835A-845A, Oct. 1, 1993.

E.D. Lipp et al., "*On-Line Monitoring Of Chlorosilane Streams By Raman Spectroscopy,*" Reprinted from Applied Spectroscopy, vol. 52, No. 1, Jan. 1998.

M.J. Pelletier et al.; "*Optical fibers enable Raman instruments to analyze industrial process probelms quickly and accurately,*" Raman Spectroscopy—Keeps Industry Under Control, Reprint: Photonics Spectra, 4 pgs., Oct. 1997.

V. Centner et al., "*Optimization in Locally Weighted Regression,*" Analytical Chemistry, vol. 70, No. 19, pp. 4206-4211, Oct. 1, 1998.

"*Principal Components Analysis,*" excerpted from PLS_Toolbox, Version 2.0 Data Analysis Manual, Eigenvector Research, Inc., pp. 32-34, 1998.

L. Markwort et al., "*Raman Imaging of Heterogeneous Polymers: A Comparison of Global versus Point Illumination,*" Applied Spectroscopy, vol. 49, No. 10, pp. 1411-1430, 1995.

I. Modric et al., "*Raman- und Infrarotspektren isotaktischer Polyalkylathylene*,*" Colloid & Polymer Sci., vol. 254, pp. 342-347, 1976.

M.G. Hansen et al., "*Real-Time Monitoring of Industrial Polymers,*"Raman Review; pp. 1-4, Mar. 1998.

S.E. Nave "*Rugged Fiber Optic Probes and Sampling Systems for Remote Chemical Analysis Via the Raman Technique,*" ISA, Paper#96-042, pp. 453-467, 1996.

M.J. Pelletier et al., "*Shining a Light on Wet Process Control,*" Semiconductor International, 4 pages, Mar. 1996.

K.P.J. Williams et al., "*Use of Micro Raman Spectroscopy for the Quantitative Determination of Polyethylene Density Using Partial Least-Squares Calibration,*" Journal of Raman Spectroscopy, vol. 26, pp. 427-433, 1995.

P. Erlich et al., "*Fundamentals of the Free-Radical Polymerization of Ethylene,*" Advances in Polymer Science, vol. 7, pp. 386-448, 1970.

A.C. Ouano et al., "*Gel Permeation Chromatography,*" Polymer Molecular Weights Part II, Chapter 6, pp. 287-378, 1975.

G. Verstrate et al., "*Near Monodisperse Ethylene-Propylene Copolymers by Direct Ziegler-Natta Polymerization*, Preparation, Characterization, Properties,*" Macromolecules, vol. 21, pp. 3360-3371, 1988.

F. Rodriguez, "*Principles of Polymer Systems 3rd Ed.,*" Hemisphere Publishing. Corp.oration, NY, pp. 155-160, 1989.

* cited by examiner

ON-LINE ANALYSIS OF POLYMER PROPERTIES FOR CONTROL OF A SOLUTION PHASE REACTION SYSTEM

CROSS REFERENCE TO RELATED APPLICATIONS

This application claims the benefit of Provisional Application No. 60/702,083 filed Jul. 22, 2005, the disclosure of which is fully incorporated herein by reference.

FIELD OF THE INVENTION

This disclosure relates to methods and systems for measuring polymeric properties and controlling polymer production, finishing, and processing processes using the measured properties.

BACKGROUND OF THE INVENTION

It is known that monomers, such as ethylene, propylene, and other olefins, may be polymerized at various temperatures and pressures. Depending on the type of polymerization process, the polymerization process pressure range may be from around 0.1 MPa to over 300 MPa and the temperature can range from about 40° C. to in excess of 300° C.

More specifically, with regard to solution polymerization, the polymerization pressure range may be from about 0.1 MPa to about 15 MPa and at a temperature of about 40° C. to about 225° C. Solution polymerization involves dissolving a monomer, such as ethylene, in a solvent and heating the dissolved mixture in a reactor under pressure in the presence of a catalyst, thereby inducing the polymerization process. Furthermore, solution processes are operated at temperatures that exceed the melting or solubilization temperature of the polymer that is produced. The solution process is operated so that both the monomer and the polymer are soluble in the reaction medium.

Exemplary of solution polymerization reactions are disclosed in the following references: U.S. Pat. No. 5,589,555 to Zboril et al., U.S. Pat. No. 5,151,474 to Lange et al., U.S. Pat. No. 4,469,853 to Mori, U.S. Pat. No. 3,725,378 to Chamberlin, and U.S. Pat. No. 4,175,169 to Beals et al.

Conventional means of controlling the polymerization process involve monitoring the physical properties of the reactive mixture within the reactor and the product stream downstream of the reactor. Typically a sample from the polymerization process is taken, however, such sampling activities are time intensive and such results are typically only available every 2 to 4 hours. With regard to commercial scale polymerization processes, many thousands of tons of product can be produced in the time span of 2 to 4 hours. As such, this sampling delay might allow a very large amount of product to be produced that is out of specification.

SUMMARY OF THE INVENTION

This disclosure relates to method and systems for analysis of reaction mixtures and product streams of solution polymerization processes. The results of the analysis may in turn be used to control the solution polymerization process and/or finishing and handling processes for the polymerization product produced in the solution polymerization processes.

In certain embodiments, the methods and systems described herein analyze reaction mixtures and/or product streams in solution polymerization processes by Raman spectroscopy analysis. The Raman spectroscopy analysis may include both compositional and characterization analysis of the reaction mixtures and product streams. The spectroscopy results can be used to provide process control feedback to adjust operating parameters of the reactor operations and/or an associated polymerization product handling and finishing processes.

DETAILED DESCRIPTION OF THE INVENTION

Figure 1:
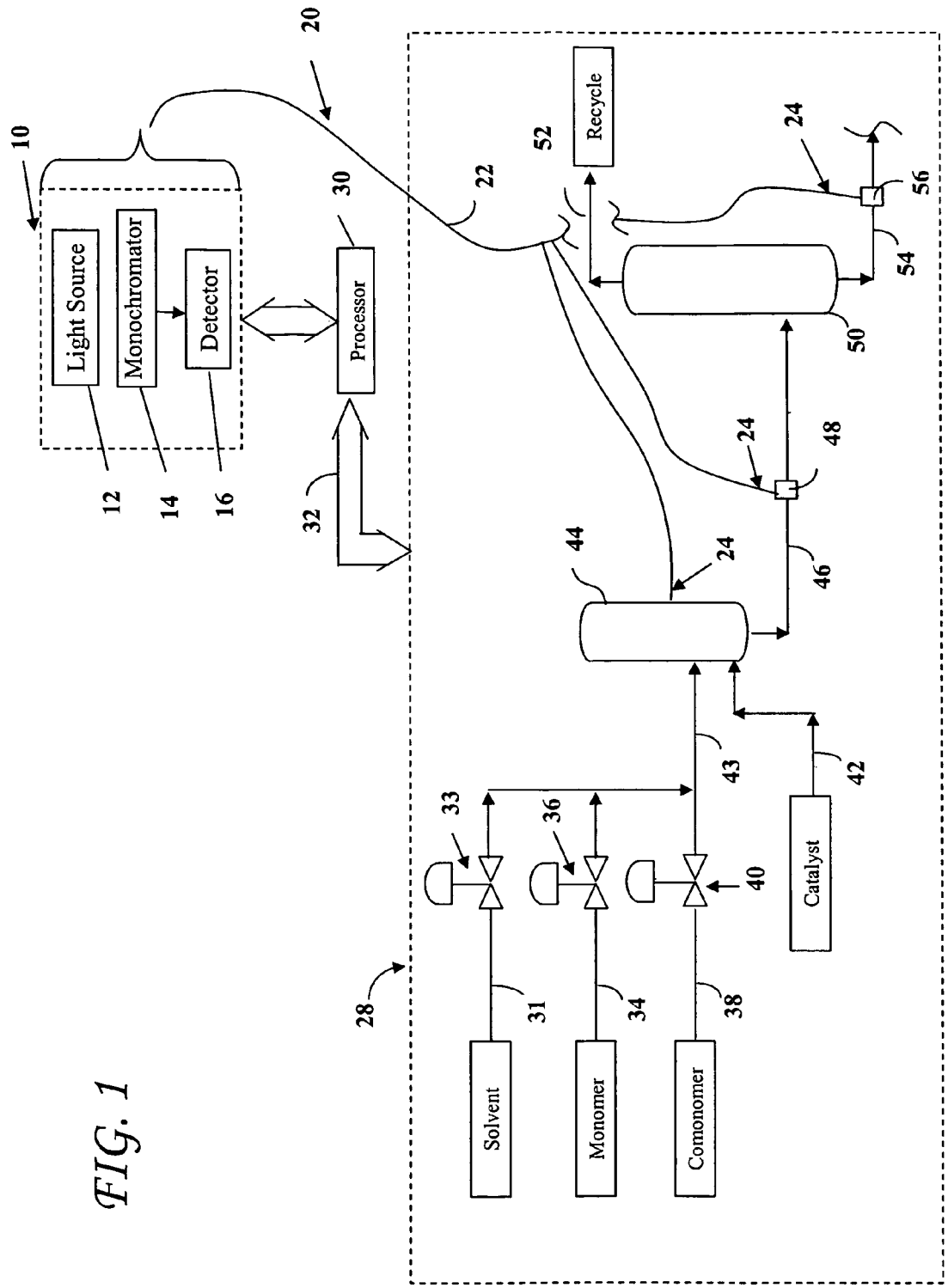
FIG. 1 is a diagram of a Raman analyzer coupled with a solution polymerization process.

This disclosure relates to the use of spectroscopic techniques to determine various properties of reaction mixtures within the reaction zone of a solution polymerization reactor and of polymer product streams downstream of the reaction zone of a solution polymerization reactor.

This disclosure also relates to using the determined properties to control the solution polymerization process. The values determined may include compositional values and a variety of characterization values. The various properties that may be analyzed will be discussed in more detail hereinafter.

Raman spectroscopy is a known analytical tool for molecular characterization, identification, and quantification. Raman spectroscopy makes use of inelastically scattered radiation from a non-resonant, non-ionizing radiation source, typically a visible or near-infrared radiation source such as a laser, to obtain information about molecular vibrational-rotational states. In general, non-ionizing, non-resonant radiation is scattered elastically and isotropically (Raleigh scattering) from a scattering center, such as a molecule. Subject to well-known symmetry and selection rules, a very small fraction of the incident radiation can be inelastically and isotropically scattered, with each inelastically scattered photon having an energy $E=h\nu_0 \pm |E_{i',j'}-E_{i,j}|$, where $h\nu_0$ is the energy of the incident photon and $|E_{i',j'}-E_{i,j}|$ is the absolute difference in energy between the final (i',j') and initial (i,j) vibrational-rotational states of the molecule. This inelastically scattered radiation is the Raman scattering, and includes both Stokes scattering, where the scattered photon has lower energy than the incident photon ($E=h\nu_0-|E_{i',j'}-E_{i,j}|$), and anti-Stokes scattering, where the scattered photon has higher energy than the incident photon ($E=h\nu_0+|E_{i',j'}-E_{i,j}|$).

Raman spectra are typically shown as plots of intensity (arbitrary units) versus "Raman shift," where the Raman shift is the difference in energy or wavelength between the excitation radiation and the scattered radiation. The Raman shift is typically reported in units of wavenumbers ($cm^{-1}$), i.e., the reciprocal of the wavelength shift in centimeters. The energy difference $|E_{i',j'}-E_{i,j}|$ and wavenumbers ($\omega$) are related by the expression $|E_{i',j'}-E_{i,j}|=hc\omega$, where h is Planck's constant, c is the speed of light in cm/s, and $\omega$ is the reciprocal of the wavelength shift in centimeters.

The spectral range of the Raman spectrum acquired is broad. However, in one embodiment, a useful range includes Raman shifts (Stokes and/or anti-Stokes) corresponding to a typical range of polyatomic vibrational frequencies, generally from about 100 $cm^{-1}$ to about 4000 $cm^{-1}$. It should be appreciated that useful spectral information is present in lower and higher frequency regions. For example, numerous low frequency molecular modes contribute to Raman scattering in the region below 100 $cm^{-1}$ Raman shift, and overtone vibrations (harmonics) contribute to Raman scattering in the region above 4000 cm$^{-1}$ Raman shift. Thus, if desired, acquisition and use of a Raman spectrum as described herein can include these lower and higher frequency spectral regions.

Conversely, the spectral region acquired can be less than all of the 100 cm$^{-1}$ to 4000 cm$^{-1}$ region. For many polymers the majority of Raman scattering intensity will be present in a region from about 500 cm$^{-1}$ to about 3500 cm$^{-1}$ or from 1000 cm$^{-1}$ to 3000 cm$^{-1}$. The region acquired can also include a variety of sub-regions that need not be contiguous. In certain embodiments, range of polyatomic vibrational frequencies acquired is about 0 cm$^{-1}$ to about 1900 cm$^{-1}$. In certain embodiments, range of polyatomic vibrational frequencies acquired is about 400 cm$^{-1}$ to about 1800 cm$^{-1}$.

As explained below, it is a particular advantage of the methods and systems described herein that Raman scattering intensity data is useful in determining properties of polymer particles without the need to identify, select, or resolve particular spectral features. Thus, it is not necessary to identify a particular spectral feature as being due to a particular mode of a particular moiety of the polymer, nor is it necessary to selectively monitor Raman scattering corresponding to a selected spectral feature. Indeed, it has been surprisingly found that such selective monitoring disadvantageously disregards a wealth of information content embedded in the spectrum that, heretofore, has generally been considered to be merely unusable scattering intensity disposed between and underlying the identifiable (and thus presumed useful) bands. Accordingly, in the methods described herein, the Raman spectral data acquired and used includes a plurality of frequency or wavelength shift, scattering intensity (x,y) measurements over relatively broad spectral regions, including regions conventionally identified as spectral bands and regions conventionally identified as interband, or unresolved regions.

The frequency spacing of acquired data can be readily determined by one skilled in the art, based on considerations of machine resolution and capacity, acquisition time, data analysis time, and information density. Similarly, the amount of signal averaging used is readily determined by one skilled in the art based on machine and process efficiencies and limitations.

In certain embodiments, the data is acquired in a continuous manner by repeating the data acquisition and analysis at designated time intervals. In specific embodiments, the data acquisition and analysis is repeated at time intervals of about 1 to about 5 minutes.

The spectral region measured can include Stokes scattering (i.e., radiation scattered at frequencies lower than the excitation frequency), anti-Stokes scattering (i.e., radiation scattered at frequencies higher than the excitation frequency), or both. Optionally, polarization information embedded in the Raman scattering signal can also be used, and one skilled in the art readily understands how to acquire Raman polarization information. However, determining polymer properties as described herein does not require the use of polarization information.

FIG. 1 provides a schematic representation of an embodiment of the methods and systems described herein. A Raman spectral system is implemented to monitor characteristics of a reaction mixture of the depicted solution polymerization process and/or the polymer product stream produced in the solution polymerization process. For the purposes of this disclosure, the reaction mixture and/or the polymer product stream shall collectively be referred to as "polymerization material". In other words, polymerization material refers to mixture of monomer, solvent, initiator/catalyst, and alternatively modifier, and polymer product forming the reaction mixture within the reactor 44. Polymerization material also refers to the unfinished and finished polymer product stream progressing through various finishing and handling processes downstream of the reactor 44, including any unreacted monomers, solvent, or other materials in the polymer product stream. In certain embodiments, the polymerization material includes from about 80 wt. % to about 96 wt. % of solvent and other non-polymeric materials and from about 4 wt. % to about 20 wt. % of polymeric material. In certain specific embodiments including multiple reactors, the first reactor may contain from about 4 wt. % to about 10 wt. % of polymeric material and the second reactor may contain from about 5 wt. % to about 20 wt. % of polymeric material. In certain embodiments, the polymerization material includes about 1 wt. % to about 25 wt. % of free monomers. In other specific embodiments, the polymerization material contains less than 1 wt. % of solid polymeric material.

The instrumentation used to collect and process Raman data includes a Raman spectrometer system 10, a transmittance system 20, a control loop 32, and a processor 30. The Raman spectrometer system 10 comprises a Raman spectrometer, the principal components of which are a light source 12, a monochromator 14, and a detector 16. Raman spectrometers are well-known analytical instruments, and thus only a brief description is provided herein. Additional detail is provided in published U.S. patent application 2004/0233425.

The Raman spectrometer system 10 includes a light source 12 that delivers excitation radiation to at least one probe 24. Scattered radiation is collected, filtered of Raleigh scattered light, and dispersed via a monochromator 14. The dispersed Raman scattered light is then imaged onto a detector 16 and subsequently processed within the processor 30, as further described below.

The excitation source and frequency can be readily determined based on considerations well known in the art. Typically, the light source 12 is a visible or near infrared laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used. It is well known that scattering, including Raman scattering, is proportional to the fourth power of the excitation frequency, subject to the practical limitation that fluorescence typically overwhelms the relatively weak Raman signal at higher frequencies. Thus, higher frequency (shorter wavelength) sources are preferred to maximize signal, while lower frequency (longer wavelength) sources are preferred to minimize fluorescence. One skilled in the art can readily determine the appropriate excitation source based on these and other considerations, such as mode stability, maintenance time and costs, capital costs, and other factors well understood in the art.

The excitation radiation can be delivered to the at least one probe 24, and the scattered radiation collected from the sample subsystem, by any convenient means known in the art, such as conventional beam manipulation optics or fiber optic cables generally designated 22. For an on-line process measurement, it is particularly convenient to deliver the excitation radiation and collect the scattered radiation fiber optically. It is a particular advantage of Raman spectroscopy that the excitation radiation typically used is readily manipulated fiber optically, and thus the excitation source can be positioned remotely from the sampling region. A particular fiber optic probe is described below; however, one skilled in the art will appreciate that the Raman spectrometer system is not limited to any particular means of radiation manipulation.

The scattered radiation is collected and dispersed by any convenient means known in the art, such as a fiber optic probe as described below. The collected scattered radiation is filtered to remove Raleigh scattering and optionally filtered to remove fluorescence, then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator 14 can be any such dispersive element, along with associated filters and beam manipulation optics.

The dispersed Raman scattering is imaged onto a detector 16. The choice of detector is easily made by one skilled in the art, taking into account various factors such as resolution, sensitivity to the appropriate frequency range, response time, etc. Typical detectors include array detectors generally used with fixed-dispersive monochromators, such as diode arrays or charge coupled devices (CCDs), or single element detectors generally used with scanning-dispersive monochromators, such as lead sulfide detectors and indium-gallium-arsenide detectors. In the case of array detectors, the detector is calibrated such that the frequency (wavelength) corresponding to each detector element is known. The detector response is delivered to the processor 30 that generates a set of frequency shift, intensity (x,y) data points which constitute the Raman spectrum.

The scattered radiation related to the polymerization material may be collected by at least one probe disposed in a variety of locations within the polymerization system 28. Exemplary locations depicted in FIG. 1 are in the reactor 44, in a product stream line 46 downstream of reactor 44, and/or in sample port 56 downstream of the reactor 44. It is understood that these probe locations are merely exemplary and that one or more probes may be located in a variety of other locations with the solution polymerization system. The at least one probe 24 delivers the excitation radiation from the light source 12 to the polymerization material, collects the scattered radiation, and delivers the scattered radiation to the monochromator 14 through the transmittance system 20.

With reference to FIG. 1, the embodiment of the solution polymerization system 28 being monitored and controlled by the Raman spectrometer system 10 is discussed in more detail. The solution polymerization system 28 comprises a solvent feed 31, a monomer feed 34, a comonomer feed 38, a reactor 44, sample ports (48, 56), and a separator system 50. As described above, the solvent feed 31 comprises a solvent that is combined with the monomer feed 34 for use in polymerizing the monomer. Exemplary suitable solvents include pentane, methyl pentane, hexane, heptane, octane, cyclopentane, cyclohexane, methylcyclohexane, toluene, and hydrogenated naptha. In certain embodiments, hexane is selected as the solvent. In certain embodiments, the solvent within the solvent feed line 31 may be heated to the appropriate reaction temperature prior to being introduced into the reactor 44. The solvent, optionally, may also include a diluents stream (not shown). Suitable diluent streams may comprise a mixture of $C_{8-10}$ saturated hydrocarbons.

The monomer feedstream may include ethylene and copolymers and terpolymers of $C_{3-12}$ olefins, and higher olefins. Optionally hydrogen injection (not shown) may be included on the monomer feedstream for introducing hydrogen into the monomer feed as is known in the art.

The comonomer feed 38 includes compounds such as 1-octene, $C_{3-12}$ alpha olefins that are unsubstituted or substituted by up to two $C_{1-6}$ alkyl radicals, $C_{8-2}$ vinyl aromatic monomers which are unsubstituted or substituted by up to two substituents selected from the group consisting of $C_{1-4}$ alkyl radicals, $C_{4-12}$ straight chained or cyclic diolefins which are unsubstituted or substituted by a $C_{1-4}$ alkyl radical. Exemplary alpha-olefins are one or more of propylene, 1-butene, 1-pentene, 1-hexene, 1-octene and 1-decene, styrene, alpha methyl styrene, and the constrained-ring cyclic olefins such as cyclobutene, cyclopentene, hexadienes, dicyclopentadiene norbornene, alkyl-substituted norbornenes, alkenyl-substituted norbornenes and the like (e.g., 5-methylene-2-norbornene and 5-ethylidene-2-norbornene, bicyclo-(2,2,1)-hepta-2,5-diene). The comonomer feedstream may be varied to produce a wide variety of copolymers, terpolymers, and higher polymers. Exemplary monomers are disclosed in U.S. Pat. No. 6,114,477 to Merrill, et al.

In the embodiment of FIG. 1 quantities of solvent, monomer, and comonomer are metered into reactor 44 via the feed lines (31, 34, 38) for polymerization of the monomer. As shown, each of these feed lines (31, 34, 38) are combined into a single reactor feed line 43 prior to being delivered to the reactor 44. Alternative embodiments include one or more of these feed lines each having its own dedicated nozzle on the reactor 44, or each feed line (31, 34, 38) having a feed nozzle (not shown) for connecting to the reactor 44. Control valves (33, 36, 40) are respectively provided on the solvent feed 31, the monomer feed 34, and the comonomer feed 38 for controlling the fluid flow through these feed lines.

In certain embodiments, the reaction temperature within the reactor 44 is maintained in a range of from about 40° C. to about 300° C. In other embodiments, the temperature is from about 80° C. to about 250° C. In still other embodiments, the temperature range is from about 100° C. to about 200° C. Generally, the reactor pressure is held at 0.1 MPa to about 15 MPa. In certain embodiments, the pressure ranges from about 0.8 MPa to about 15 MPa and the temperature is from about 35° C. to about 95° C. In additional embodiments, the pressure is from about 12 MPa to about 15 MPa and the temperature is from about 80° C. to about 205° C.

Typically, the polymerization reaction will be exothermic and the reactor will be chilled or cooled in accordance with known methods to assure that temperatures do not exceed those reasonably suitable for the polymer being produced. The monomer purification prior to introduction into the reactor 44 may be conducted within standard practices in the art, e.g., molecular sieves, alumina beds, and oxygen removal catalysts are used for the purification of the monomer. The solvent itself as well, that can be comprised of hexane, toluene, or mixtures thereof, are similarly treated.

Further, optionally, the solvent may be comprised of a mixture of an olefin, such as propylene, hexane, a diene, and an activator solution. Yet further, optionally, a scavenger solution may be included with the solvent for absorption of impurities and/or to reduce or eliminate any impurities that could adversely affect the performance of the catalyst. Examples of suitable scavenger compounds may be found in U.S. Pat. No. 5,696,213 to Schiffino et al.

The reactor 44 may be any type of solution polymerization reactor. Alternatively, the reactor 44 may be comprised of two or more reactors. In certain embodiments, one or more catalysts or initiators are delivered to the reactor 44 via the catalyst feed 42. In other embodiments, the catalysts or initiators delivered are combined with the monomer/solvent/comonomer mixture to promote polymerization of the monomer within the reactor 44. Exemplary catalysts include Ziegler- Natta catalysts, chromium catalysts, vanadium catalysts, and metallocene catalysts. Exemplary initiators include free radical initiators that may include oxygen or peroxidic compounds. A list of exemplary peroxidic compounds is disclosed in U.S. Pat. No. 4,175,169 issued to Beals et al.

While the monomer may be any molecule or molecules capable of addition polymerization by either a free-radical mechanism, a coordination catalytic mechanism, or metallocene catalysis, a particularly suitable monomer used in solution polymerizations is ethylene. Other exemplary monomers include propylene and hexene. Of course, it is understood that any number of different monomers may be used, including comonomers and termonomers.

Within the reactor 44 the process of converting the monomer into a polymer occurs by processes well known in the art. For example, in one known process, monomers are stripped of at least one of their associated hydrogen atoms that in turn allows monomeric bonding thereby forming polymeric chains comprised of these monomers. A step-by-step analysis of this process reveals certain intermediate polymeric compounds that can exist during the process of polymerization.

The reaction process within the reactor 44 produces a reaction mixture comprising a solvent, a polymeric product, unreacted monomer, and some small portion of intermediate compounds that have been only partially polymerized. The primary constituents of the reaction mixture are transferred from the reactor 44 to the separator system 50 via the reactor discharge line 46. The polymeric product is separated from the solvent and unreacted monomer within the separator system 50. Although it is not depicted in FIG. 1, it is understood that recycle stream 52 may be analyzed using the methods and systems described herein. The polymeric product is discharged from the separator system 50 through a product stream line 54 for extrusion and/or other finishing process steps. The polymer product stream removed from the separator system 50 may be vented to produce an offgas stream (not shown). In certain embodiments, a probe may be provided in the offgas stream or recycle solvent stream to provide a compositional analysis of this stream.

Compositional values and a variety of characterization values for the polymerization material may be determined using the methods and systems described herein Exemplary values that may be determined for the polymeric materials contained in the polymerization material include melt index, density, viscosity, molecular weight, molecular weight distribution, additive concentrations, weight ratios of different polymers making up the polymerization material, die swell, melt flow rate, monomer content, comonomer content, modifier content, catalyst concentration, Mooney viscosity, and combinations thereof. In certain embodiments, the values determined for the polymerization material determined are melt index, density, viscosity, melt flow rate, monomer content, comonomer content, termonomer content, the content of monomers higher than termonomers, and combinations thereof. In other embodiments, the determined values for the polymerization material are melt index, density, viscosity, monomer content, and combinations thereof. In still other embodiments, the determined values for the polymerization material are melt index and density, and combinations thereof.

Monitoring and evaluation of these characteristics can be accomplished on-line and real time with Raman spectroscopy during the polymerization process. The Raman monitoring can occur within and/or downstream of the reactor 44, as well as before and after the separator process system 50. These monitoring options are illustrated in FIG. 1 where Raman probes 24 are shown inserted within the reactor 44, in the reactor discharge line 46, and in a sample port 56 in the polymer product stream line 54 exiting the separator system 50. The sample port 56 may be a simple aperture formed within the product stream lines 54 or can be a dedicated length of piping formed specifically to receive or house a Raman probe 24.

In certain embodiments in which a probe is located in a sample stream, the sampling apparatus may be designed to continuously extract a slip stream of the desired polymerization material from the solution polymerization process and direct the stream to a probe and then return the extracted portion of the polymerization material to the solution process. Generally, it is desirable to conduct the analysis on a large amount of product, therefore, it is desirable to maintain the extracted portion of the polymerization material as a continuously flowing slip stream out of and back into the solution process. A gear pump may be implemented to ensure that the slip steam flows continuously past the probe. In certain embodiments, at least one gear pump may be used to maintain the slip stream at a velocity of about 2 m/s to about 10 m/s to ensure that the polymerization material provides sufficient friction to maintain the probe tip in a clean condition. In other embodiments, at least one gear pump may be used to maintain the slip stream at a velocity of about 3 m/s to about 8 m/s to ensure that the polymerization material provides sufficient friction to maintain the probe tip in a clean condition. In additional embodiments, at least one gear pump may be used to maintain the slip stream at a velocity of about 3 m/s to about 5 m/s to ensure that the polymerization material provides sufficient friction to maintain the probe tip in a clean condition.

In certain embodiments, the sampling system may be selectively isolated from the solution polymerization process through the use of one or more valves that may be selectively open and closed as desired for sampling, discontinuing the sampling, or maintenance of the sampling system.

Solution polymerization processes present unique temperature and pressure environments in which to conduct spectroscopic analysis as described herein. In certain embodiments, the temperature surrounding the probe should be accurately determined to compensate for the shift in the scattered radiation associated with the measured temperature to ensure accurate analysis.

The high degree of homogeneity of the polymerization material in solution phase reaction systems may provide an opportunity to optimize the position of the focal point of the analysis probe to provide more accurate analysis. Specifically, a high level of homogeneity may allow implementation of an analysis probe with the focal point extended well into the sample to provide more accurate analysis. Generally, if the polymerization material is in a homogeneous state, a more accurate analysis will be obtained if the focal point of the analysis probe is extended well into the sample. Correspondingly, if the polymerization material is in a relatively non-homogeneous state, the focal point of the analysis probe should be located just beyond the window to ensure more accurate analysis.

To provide a more accurate analysis of polymerization materials in solution phase polymerization systems having a relatively high degree of homogeneity, in certain exemplary embodiments, an analysis probe having a focal point about 400 µm to 700 µm beyond the probe window is used to analyze solution phase polymerization material. In still other exemplary embodiments, an analysis probe having a focal point about 500 µm to 650 µm beyond the probe window is used to analyze solution phase polymerization material. In additional exemplary embodiments, an analysis probe having a focal point about 575 µm to about 625 µm beyond the probe window is used to analyze solution phase polymerization material. In more particular embodiments, an analysis probe having a focal point about 600 µm beyond the probe is used to analyze solution phase polymerization material. It is also thought the solution phase systems provide an environment in which analyzer probes used in the systems and methods described herein are less susceptible to fouling.

Under certain circumstances in certain portions of the solution phase systems, the polymerization material may be relatively nonhomogeneous. To provide a more accurate analysis under such conditions, in certain exemplary embodiments, an analysis probe having a focal point about 50 µm to about 200 µm beyond the probe window is used to analyze solution phase polymerization material. In other exemplary embodiments, an analysis probe having a focal point about 50 µm to about 150 µm beyond the probe window is used to analyze solution phase polymerization material. In additional exemplary embodiments, an analysis probe having a focal point about 75 µm to about 100 µm beyond the probe window is used to analyze solution phase polymerization material. In more particular exemplary embodiments, an analysis probe having a focal point about 75 µm beyond the probe window is used to analyze solution phase polymerization material.

In solution phase systems as described herein, it may be necessary to compensate for a relatively high level of signal interference (noise). This noise may be attributable to signals generated by high levels of solvent and/or waxes present in the polymerization material. Generally, in such systems, it is difficult to improve the signal-to-noise ratio because of shot noise limits. However, the analysis may be altered to compensate for the noise and to conduct an accurate analysis. One manner of compensation is to use longer data sampling periods to generate more pronounced desired signals to distinguish the signal over the noise.

It is understood that the methods and systems described herein may be utilized by analyzing only the reaction mixture within the reactor 44, analyzing the polymer product stream within sample port 48, analyzing the polymer product stream within sample port 56, or combinations thereof.

In one embodiment, the processor 30 compares the results of the Raman analysis with baseline data to ensure that the polymerization material of the polymerization system 28 is within acceptable operating specifications. Should the processor 30 detect an excursion from these specifications, the processor 30 may be programmed to provide control commands to the polymerization system 28. The control commands may be delivered to the polymerization system 28 via the control loop 32. The processor 30 may be programmed to recognize excursions from specified operating parameters and take necessary corrective action. It is well within the scope of one skilled in the art to develop a suitable control loop 32 for relaying control commands from the processor 30 to the polymerization system 28.

As discussed above, the processor 30 affects operation of the polymerization system 28 by directing control commands to the polymerization system 28 via the control loop 32. For example, the calculated reaction material properties are compared to target properties, and at least one reactor parameter in the polymerization system 28 is adjusted based on the deviation between the calculated and target product properties. The at least one polymerization process parameter may include monomer concentration, comonomer concentration, catalyst concentration, cocatalyst concentration, reactor temperature, reactor pressure, the ratio of monomer feeds, the ratio of hydrogen to monomer, modifier concentration, recycle gas concentrations, and combinations thereof. For example, if the particular property determined is density, a reactor parameter can be adjusted to increase density, such as, for example, reducing the comonomer feed rate and/or increasing the monomer feed rate. In other embodiments, the at least one polymerization process parameter that may be adjusted is selected from monomer concentration, comonomer concentration, additive concentration, modifier concentration, reactor pressure, reactor temperature, and combinations thereof. In still other embodiments, the at least one polymerization process parameter that may be adjusted is selected from monomer concentration, reactor pressure, reactor temperature, and combinations thereof.

As noted above, the excitation radiation can be delivered to and collected from the polymerization material by any convenient means, such as using conventional optics or fiber optic cables. In certain embodiments, the transmittance system 20 includes a probe 24 connected to the Raman spectrometer system 10 via cables 22.

Figure 2:
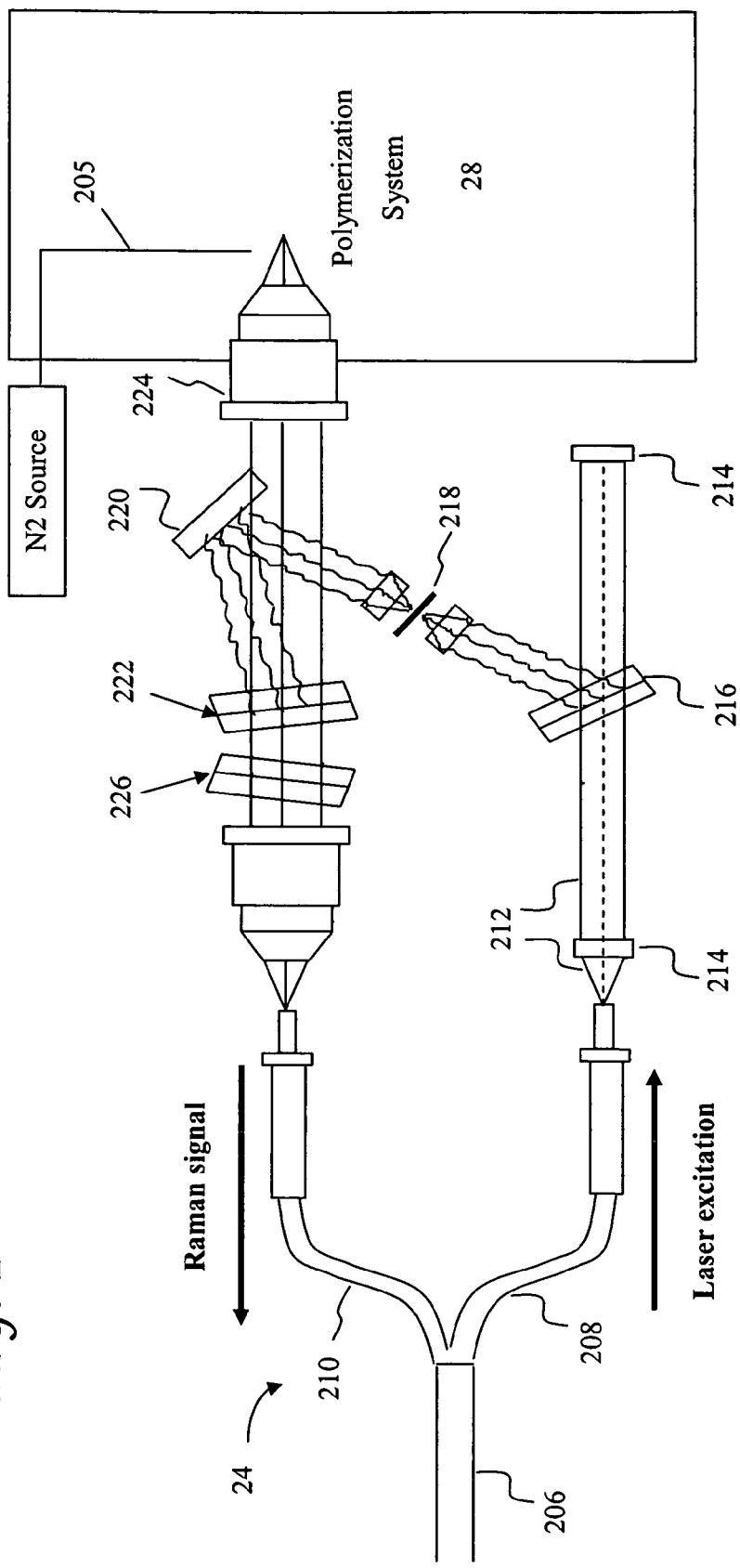
FIG. 2 depicts a fiber optic Raman probe in accordance with one embodiment of the methods and systems described herein.

FIG. 2 is a diagram of one embodiment of a fiber optic probe useful in the systems and processes described herein. The probe includes a fiber optic bundle 206 including one or more fiber optic cables 208 carrying the excitation radiation from the excitation source toward the polymeric compound, and one or more fiber optic cables 210 carrying the collected scattered radiation from the polymeric compound. Fiber optic cables 208 are in optical communication with the light source 12 (not shown in FIG. 2), and fiber optic cables 210 are in optical communication with the monochromator 14 (not shown in FIG. 2). The excitation and scattered radiation can be manipulated using well-known techniques. Thus, it should be appreciated that the particular optical setup shown in FIG. 2 is merely exemplary. Excitation radiation 212 is directed via optics 214 to a holographic grating 216 and spatial filter 218 to remove silica Raman due to the fiber optic cable, then directed via mirror 220 and beam combiner 222 to sampling optics (not shown) within probe head 224. Scattered radiation is collected via the sampling optics and directed through beam combiner 222, a notch filter 226 to remove the Raleigh scattered radiation, and into fiber optic cables 210.

Because static charge may build up on the probe head 224 to dissipate static charge, an optional grounding strap (not shown) can be used to ground the probe head 224.

Optionally, an inert gas or solvent flow is provided via conduit 205. The inert gas or solvent, such as nitrogen or hexane, is directed via conduit 205 to provide a gas flow across the probe head 224 to reduce the incidence of probe fouling on the probe head 224.

Referring to FIG. 1, the processor 30 receives signals from the detector 16. The processor 30 can comprise a computer capable of storing and processing the Raman data. In one embodiment described above, the processor 30 controls the motion of the sampling probe. In yet another embodiment, the comparison of target to calculated values is relied on for adjusting the control of the polymerization system 28.

With respect to the various ranges set forth herein, any upper limit recited may, of course, be combined with any lower limit for selected sub-ranges.

All patents and publications, including priority documents and testing procedures, referred to herein are hereby incorporated by reference in their entireties.

Although the methods and systems described herein and their advantages have been described in detail, it should be understood that various changes, substitutions, and alterations could be made without departing from the spirit and scope of the inventions described herein as defined by the following claims.

What is claimed is:

1. A method of monitoring a solution polymerization process comprising:
   (a) forming a polymerization material comprising: (i) a reaction mixture comprising monomer, solvent, and polymer product within a reaction zone and (ii) polymer product downstream of the reaction zone;
   (b) maintaining the temperature within the reaction zone from about 40° C. to about 300° C. and maintaining the pressure within the reaction zone from about 0.1 MPa to about 15 MPa;
   (c) irradiating at least a portion of the polymerization material;
   (d) measuring the energy shift experienced by the at least a portion of the polymerization material due to the step of irradiating; and
   (e) determining a characteristic of the at least a portion of the polymerization material based on the energy shift; wherein the at least one analysis probe has a focus point of about 50 to 200 μm for non-homogeneous polymerization materials and a focus point of about 400 to 700 μm for homogeneous polymerization materials.

2. The method of claim 1, wherein the characteristic of the at least a portion of the polymerization material is selected from the group consisting of melt index, density, viscosity, molecular weight, molecular weight distribution, additive concentration, weight ratios of different polymers making up the polymerization material, die swell, melt flow rate, monomer content, comonomer content, modifier content, catalyst concentration, Mooney viscosity, and combinations thereof.

3. The method of claim 2, wherein the steps (c), (d), and (e) are conducted using at least one analysis probe and Raman spectroscopy.

4. The method of claim 3, comprising repeating steps (c), (d), and (e).

5. The method of claim 4, wherein the frequency of repeating steps (c), (d), and (e) ranges from about 1 minute to about 5 minutes.

6. The method of claim 5, wherein the reaction zone is maintained at a temperature of about 80° C. to about 250° C. and a pressure of about 0.8 MPa to about 15 MPa.

7. The method of claim 6, wherein the step of irradiation comprises irradiating the polymerization material with a light source having a wavelength of from about 400 cm$^{-1}$ to about 1800 cm$^{-1}$.

8. The method of claim 7, wherein a first signal representative of the characteristic determined in step (e) is generated and transmitted to a processor.

9. The method of claim 8 comprising generating at least one control command with the processor and transmitting the control command from the processor to the polymerization process.

10. The method of claim 9, wherein the at least one control command provided to the solution polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

11. The method of claim 10, wherein the solution polymerization process is a continuous process.

12. The method of claim 11, wherein the characteristic of the at least a portion of the polymerization material is selected from the group consisting of melt index, density, viscosity, melt flow rate, monomer content, comonomer content, and combinations thereof.

13. The method of claim 12, wherein the at least one control command provided to the polymerization process relates to control of a parameter selected from the group consisting of monomer concentration, catalyst concentration, reactor temperature, and combinations thereof.

14. The method of claim 1, wherein the at least a portion of the polymerization material is irradiated in at least two locations and the characteristic generated is generated for the polymerization material at the at least two locations.

15. The method of claim 9, wherein one or more of the following is satisfied:
   a) the at least a portion of the polymerization material is at least a portion of the reaction mixture and the at least a portion of the reaction mixture is irradiated within the reaction zone; and
   b) the at least a portion of the polymerization material is at least a portion of the polymer product downstream of the reaction zone and the at least one analysis probe has a focus point of about 50 μm to about 150 μm.

16. The method of claim 8, wherein the at least one control command provided to the solution polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

17. The method of claim 16, wherein the solution polymerization process is a continuous process.

18. The method of claim 17, wherein the characteristic of the at least a portion of the polymerization material is selected from the group consisting of melt index, density, viscosity, melt flow rate, monomer content, comonomer content, and combinations thereof.

19. The method of claim 18, wherein the at least one control command provided to the polymerization process relates to control of a parameter selected from the group consisting of monomer concentration, catalyst concentration, reactor temperature, and combinations thereof.

20. The method of claim 19, wherein the characteristic of the at least a portion of the polymerization material is selected from the group consisting of melt index, density, and combinations thereof.

21. The method of claim 19, wherein the at least a portion of the polymerization material is irradiated in at least two locations and the characteristic generated is generated for the polymerization material at the at least two locations.

22. The method of claim 9, wherein the at least a portion of the polymerization material is at least a portion of the polymer product downstream of the reaction zone and the at least one analysis probe has a focus point of about 50 μm to about 150 μm.

23. The method of claim 15, wherein the reaction zone is maintained at a temperature of about 80° C. to about 205° C. and a pressure of about 12 MPa to about 15 MPa.

24. The method of claim 23, wherein the at least one control command provided to the solution polymerization process relates to control of a parameter selected from the group consisting of monomer concentration, comonomer concentration, catalyst concentration, cocatalyst concentration, reactor temperature, the ratio of monomer feeds, the ratio of hydrogen to monomer, and combinations thereof.

25. The method of claim 24, wherein the solution polymerization process is a continuous process.

26. The method of claim 25, wherein the characteristic of the at least a portion of the polymerization material is selected from the group consisting of melt index, density, viscosity, melt flow rate, monomer content, comonomer content, and combinations thereof.

27. The method of claim 26, wherein the at least one control command provided to the polymerization process relates to control of a parameter selected from the group consisting of monomer concentration, catalyst concentration, reactor temperature, and combinations thereof.

28. The method of claim 27, wherein the characteristic of the at least a portion of the polymerization material is selected from the group consisting of melt index, density, and combinations thereof.

29. The method of claim 28, wherein the at least a portion of the polymerization material is irradiated in at least two locations and the characteristic generated is generated for the polymerization material at the at least two locations.

* * * * *